US010369177B2

(12) United States Patent
Tsubouchi et al.

(10) Patent No.: US 10,369,177 B2
(45) Date of Patent: Aug. 6, 2019

(54) AGENT FOR IMPROVING OR MAINTAINING QOL

(71) Applicant: OTSUKA PHARMACEUTICAL CO., LTD., Chiyoda-ku, Tokyo (JP)

(72) Inventors: Mina Tsubouchi, Osaka (JP); Takao Saito, Osaka (JP); Masamichi Toba, Osaka (JP); Noriyuki Kouda, Osaka (JP); Shoji Shinkai, Itabashi-ku (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 20 days.

(21) Appl. No.: 15/488,623

(22) Filed: Apr. 17, 2017

(65) Prior Publication Data

US 2017/0216379 A1 Aug. 3, 2017

Related U.S. Application Data

(62) Division of application No. 14/008,325, filed as application No. PCT/JP2012/058145 on Mar. 28, 2012, now Pat. No. 9,623,054.

(30) Foreign Application Priority Data

Mar. 31, 2011 (JP) ................................ 2011-080814

(51) Int. Cl.
*A61K 35/747* (2015.01)
*A23L 2/52* (2006.01)
*A61K 35/74* (2015.01)
*A23L 33/135* (2016.01)

(52) U.S. Cl.
CPC .............. *A61K 35/747* (2013.01); *A23L 2/52* (2013.01); *A23L 33/135* (2016.08); *A61K 35/74* (2013.01); *A23V 2002/00* (2013.01)

(58) Field of Classification Search
None
See application file for complete search history.

(56) References Cited

U.S. PATENT DOCUMENTS

2006/0182727 A1 8/2006 Yamahira et al.
2010/0159072 A1 6/2010 Endo et al.

FOREIGN PATENT DOCUMENTS

| EP | 1 854 363 B1 | 7/2010 |
| EP | 1 661 983 B1 | 1/2011 |
| JP | 2010-222329 A | 10/2010 |
| WO | 2005/019438 A1 | 3/2005 |
| WO | 2006/090729 A1 | 8/2006 |

OTHER PUBLICATIONS

The Communication Pursuant to Rule 114(2) EPC (Third Party Observation) dated Oct. 6, 2015 for EP Patent Application No. 12762904.6.
Communication dated Oct. 27, 2016 from the State Intellectual Property Office of the P.R.C. in counterpart Application No. 201280014484.4.
Communication for EP 12762904.6 dated Oct. 6, 2014, with Supplementary European Search Report (dated Sep. 25, 2014).
International Search Report for PCT/JP2012/058145 dated May 1, 2012.
Ji-Shan et al., "The Production Techniques of Sterilized Lactic Acid Bacterial Beverage", Storage and Process, 4(1):16(2004).
Kaiyadeva; Kaiyadevanighantau—(Pathyapathyavibodhakah) Edited and translated by P.V. Sharma and Guru Prasad Sharma, Chaukhambha Orientalia, Varanasi, Edn. 1st, 1979 p. 363 Formulation ID: RS6/789A Formulation Name: Ghrta Uddhrta Takra.
Liang et al., "Study of Active bacteria Preparation on Antifatigue in Mice", Journal of Shandong Agricultural university (Natural Science), 2004, 35 (2), pp. 224-226.
Logan et al., "Chronic fatigue syndrome: lactic acid bacteria may be of therapeutic value", Medical Hypothesis, 60(6):915-923 (2003).
Mahendra Bhaugika; Dhanvantarinighantauh—Edited by P.V. Sharma; Translated by Guru Prasad Sharma; Chaukhambha Orientalia, Varanasi, Edn. 3rd, 2002 p. 209 Formulation ID: AK12/523B Formulation Name: Kurcikadi Guna.
Manthana Bhairava; Anandakandah—Edited with Tamil translation by S.V. Radhakrishna Sastri, T.M.S.S.M. Library, Tanjore, Madras, Edn. 1st 1952 p. 214 Formulation ID: RS13/290 Formulation Name: Hastikarni Pancanga Kalpah.
Qing-Yuan et al. "The Health Effects and Development of Probiotics", Agricultural Biotechnology Industry Quarterly, 11:60-68 (2007).
Sciya Makino et al., "Reducing the Risk of Infection in the Elderly by Dietary Intake of Yoghurt Fermented with *Lactobacillus delbrueckii* ssp. bulgaric OLL1073R-1", British Journal of Nutrition, 2010, pp. 998-1006, vol. 104, No. 7.
Sodhala; Gadanigrahah ed,Ganga Sahaya Pandeya & Com.—Indradeva Tripathi, Part-3(Salakya-Pancakarma Khanda) Chaukhamba Sanskrit Sansthan(Varanasi) Ed. 3rd 1999 p. 699-700 Formulation ID: RG2/1586A Formulation Name: Hemanta Ritu Pathya.
Sullivan et al., "Effective of supplement with lactic-acid producing bacteria on fatigue and physical activity in patients with chronic fatigue syndrome", Nutrition Journal, 8(1):4 (1-6) (2009).
Toshitaka Odamaki et al., "Probiotics no Kino Kenkyu I BB536 Haigo Yogurt no Sugi Kafunsho Shojo Kaizen Koka Oyobi sono Sayo Kijo no Kento", Shokuhin Kako, 2005, pp. 33-39, vol. 48, No. 18.
Vagbhata; Astanga Samgraha—(commentary by Indu), part-I(KA) ; Central Council for Research in Ayurveda & Siddha, New Delhi, 1991. [Time of origin 5-10th century] p. 61 Formulation ID: AT /2119 Formulation Name: Kilatadiksiravikaragunaah.

(Continued)

*Primary Examiner* — Michelle F. Paguio Frising
(74) *Attorney, Agent, or Firm* — Sughrue Mion, PLLC

(57) ABSTRACT

[Object]
An object of the present invention is to provide a QOL improving or sustaining agent, a physical health improving or sustaining agent, a vitality improving or sustaining agent, a fatigue recovery or alleviating agent, or an anti-fatigue agent.
[Method for Achieving the Object]
A QOL improving or sustaining agent, a physical health improving or sustaining agent, a vitality improving or sustaining agent, a fatigue recovery or alleviating agent, or an anti-fatigue agent containing *Lactobacillus* ONRICb0240 (FERM BP-10065).

4 Claims, No Drawings

(56) References Cited

OTHER PUBLICATIONS

Yoichi Fukushima, "Probiotics and Natural Defense Function of the Host", Bioscience Microflora, 2007, pp. 1-10, vol. 26, No. 1.
Shimosato, T., Tomida, K., and Otani, H., "Effect of Lactobacillus pentosus ONRIC b0240 on Intestinal IgA Production in Mice Fed Differing Levels of Protein", Journal of Agricultural and Food Chemistry 2011, vol. 59, pp. 2646-2651.
Emery, P. W., "Metabolic changes in malnutrition", Eye 2005, vol. 19, pp. 1029-1034.
Jun-Hong et al., "Experimental Research on Anti-Fatigue Effect of Fermented Milk (Yogurt) on Mice", Modern Preventive Medicine, 34(16):3060-3062 (2007).

AGENT FOR IMPROVING OR MAINTAINING QOL

CROSS REFERENCE TO RELATED APPLICATIONS

This is a Divisional Application of U.S. application Ser. No. 14/008,325 filed Sep. 27, 2013, which is a National Stage of International Application No. PCT/JP2012/058145 filed Mar. 28, 2012, claiming priority to Japanese Patent Application No. 2011-080814 filed Mar. 31, 2011. The entire disclosures of the prior applications are considered part of the disclosure of the accompanying divisional application, and are hereby incorporated by reference.

TECHNICAL FIELD TO WHICH THE INVENTION PERTAINS

The present invention relates to a Quality of Life (QOL) improving or sustaining agent.

BACKGROUND ART

In the present day, great value is placed on Quality of Life (QOL) in all fields. QOL is a concept that takes into consideration affluence in the physical aspect and the mental aspect, and it is desirable to maintain both of these aspects in fine condition.

However, the physical aspect, i.e., physical health, is often impaired in everyday life due to disarray in lifestyle habits including insufficient rest and sleep, irregular meal patterns, and lack of exercise. One can recover from declined physical health normally by resting, sleeping, or the like; however, when the decline in physical health becomes seriously advanced or is prolonged, it becomes difficult to recover therefrom, resulting in problems such as easily being fatigued, chronic fatigue, or the like. Such decline in physical health brings inconvenience to everyday life, becomes a stress for some people, and may result in impairment of mental health. Therefore, maintaining physical health in fine condition is very important.

In addition, the present situation is that such decline in physical health is occurring not only in elderly people whose physical strength is in decline, but also in younger people. Therefore, there is a strong call for maintaining physical health in fine condition regardless of the age.

Meanwhile, *Lactobacillus* ONRICb0240 (FERM BP-10065) strain, which is one type of lactobacilli, is known to have a mucosal immunization activation effect, in particular, is known to have an IgA production stimulatory effect (Patent Literature 1 and 2), and is known to have an anti-avian flu antibody production stimulatory effect (Patent Literature 3). However, there have not been any reports about this *lactobacillus* regarding an improvement in physical health or an improvement in QOL based thereon.

PRIOR ART

Patent Literature

[PTL 1] EP1661983B1
[PTL 2] EP1854363B1
[PTL 3] Japanese Laid-Open Patent Publication No. 2010-222329

DETAILED DESCRIPTION OF THE INVENTION

Problem to be Solved by the Invention

An object of the present invention is to provide a QOL improving or sustaining agent, in particular, a physical health improving or sustaining agent, using *Lactobacillus* ONRICb0240 (FERM BP-10065) strain (hereinafter, also represented as *Lactobacillus* b0240 strain). Furthermore, another object of the present invention is to provide a vitality improving or sustaining agent, a fatigue recovery or alleviating agent, or an anti-fatigue agent using the *Lactobacillus* ONRICb0240 strain.

Means for Solving the Problem

The present inventors have conducted thorough research in order to solve the above described problem, and discovered that the *Lactobacillus* ONRICb0240 strain has an effect of enhancing physical health, in particular, an effect of enhancing vitality such that fatigue is not likely to occur, and an effect of lessening or alleviating fatigue. In addition, the present inventors have discovered that, as a result of such effects, physical health can be improved and thereby QOL can be improved from the physical aspect. The present invention has been accomplished based on these findings and additional studies. More specifically, the present invention provides the invention set forth in the following.

(1) QOL Improvement or Sustainment

Item 1-1. A QOL improving or sustaining agent containing *Lactobacillus* ONRICb0240 (FERM BP-10065).

Item 1-2. The QOL improving or sustaining agent according to item 1-1, containing not less than $10^4$ cells/mg of the *Lactobacillus* ONRICb0240 (FERM BP-10065).

Item 1-3. The QOL improving or sustaining agent according to item 1-1, containing not less than $10^4$ cells of the *Lactobacillus* ONRICb0240 (FERM BP-10065).

Item 1-4. A food, beverage, or pharmaceutical preparation containing the QOL improving or sustaining agent according to any one of items 1-1 to 1-3.

Item 1-5. A QOL improving or sustaining method for an animal that requires improvement or sustainment of QOL, the method comprising a step of causing the animal to take in the QOL improving or sustaining agent according to any one of items 1-1 to 1-3.

Item 1-6. A QOL improving or sustaining method for an animal that requires improvement or sustainment of QOL, the method comprising a step of causing the animal to take in the food, beverage, or pharmaceutical preparation according to item 1-4.

Item 1-7. Use of *Lactobacillus* ONRICb0240 (FERM BP-10065) for manufacturing a QOL improving or sustaining agent.

(2) Physical Health Improvement or Sustainment

Item 2-1. A physical health improving or sustaining agent containing *Lactobacillus* ONRICb0240 (FERM BP-10065).

Item 2-2. The physical health improving or sustaining agent according to item 2-1, containing not less than $10^4$ cells/mg of the *Lactobacillus* ONRICb0240 (FERM BP-10065).

Item 2-3. The physical health improving or sustaining agent according to item 2-1, containing not less than $10^4$ cells of the *Lactobacillus* ONRICb0240 (FERM BP-10065).

Item 2-4. A food, beverage, or pharmaceutical preparation containing the physical health improving or sustaining agent according to any one of items 2-1 to 2-3.

Item 2-5. A physical health improving or sustaining method for an animal that requires improvement or sustainment of physical health, the method comprising a step of causing the animal to take in the physical health improving or sustaining agent according to any one of items 2-1 to 2-3.

Item 2-6. A physical health improving or sustaining method for an animal that requires improvement or sustainment of physical health, the method comprising a step of causing the animal to take in the food, beverage, or pharmaceutical preparation according to item 2-4.

Item 2-7. Use of *Lactobacillus* ONRICb0240 (FERM BP-10065) for manufacturing a physical health improving or sustaining agent.

(3) Vitality Improvement or Sustainment

Item 3-1. A vitality improving or sustaining agent containing *Lactobacillus* ONRICb0240 (FERM BP-10065).

Item 3-2. The vitality improving or sustaining agent according to item 3-1, containing not less than $10^4$ cells/mg of the *Lactobacillus* ONRICb0240 (FERM BP-10065).

Item 3-3. The vitality improving or sustaining agent according to item 3-1, containing not less than $10^4$ cells of the *Lactobacillus* ONRICb0240 (FERM BP-10065).

Item 3-4. A food, beverage, or pharmaceutical preparation containing the vitality improving or sustaining agent according to any one of items 3-1 to 3-3.

Item 3-5. A vitality improving or sustaining method for an animal that requires improvement or sustainment of vitality, the method comprising a step of causing the animal to take in the vitality improving or sustaining agent according to any one of items 3-1 to 3-3.

Item 3-6. A vitality improving or sustaining method for an animal that requires improvement or sustainment of vitality, the method comprising a step of causing the animal to take in the food, beverage, or pharmaceutical preparation according to item 3-4.

Item 3-7. Use of *Lactobacillus* ONRICb0240 (FERM BP-10065) for manufacturing a vitality improving or sustaining agent.

(4) Fatigue Recovery or Alleviation

Item 4-1. A fatigue recovery or alleviating agent containing *Lactobacillus* ONRICb0240 (FERM BP-10065).

Item 4-2. The fatigue recovery or alleviating agent according to item 4-1, containing not less than $10^4$ cells/mg of the *Lactobacillus* ONRICb0240 (FERM BP-10065).

Item 4-3. The fatigue recovery or alleviating agent according to item 4-1, containing not less than $10^4$ cells of the *Lactobacillus* ONRICb0240 (FERM BP-10065).

Item 4-4. A food, beverage, or pharmaceutical preparation containing the fatigue recovery or alleviating agent according to any one of items 4-1 to 4-3.

Item 4-5. A fatigue recovery or alleviating method for an animal that requires fatigue recovery or alleviation, the method comprising a step of causing the animal to take in the fatigue recovery or alleviating agent according to any one of items 4-1 to 4-3.

Item 4-6. A fatigue recovery or alleviating method for an animal that requires fatigue recovery or alleviation, the method comprising a step of causing the animal to take in the food, beverage, or pharmaceutical preparation according to item 4-4.

Item 4-7. Use of *Lactobacillus* ONRICb0240 (FERM BP-10065) for manufacturing a fatigue recovery or alleviating agent.

(5) Anti-Fatigue

Item 5-1. An anti-fatigue agent containing *Lactobacillus* ONRICb0240 (FERM BP-10065).

Item 5-2. The anti-fatigue agent according to item 5-1, containing not less than $10^4$ cells/mg of the *Lactobacillus* ONRICb0240 (FERM BP-10065).

Item 5-3. The anti-fatigue agent according to item 5-1, containing not less than $10^4$ cells of the *Lactobacillus* ONRICb0240 (FERM BP-10065).

Item 5-4. A food, beverage, or pharmaceutical preparation containing the anti-fatigue agent according to any one of items 5-1 to 5-3.

Item 5-5. An anti-fatigue method for an animal that requires anti-fatigue, the method comprising a step of causing the animal to take in the anti-fatigue agent according to any one of items 5-1 to 5-3.

Item 5-6. An anti-fatigue method for an animal that requires anti-fatigue, the method comprising a step of causing the animal to take in the food, beverage, or pharmaceutical preparation according to item 5-4.

Item 5-7. Use of *Lactobacillus* ONRICb0240 (FERM BP-10065) for manufacturing an anti-fatigue agent.

Effect of the Invention

With the QOL improving or sustaining agent of the present invention, QOL on which great value is placed in the present day can be improved or sustained. In particular, the *Lactobacillus* ONRICb0240 strain has an effect of enhancing physical health. With this, the QOL improving or sustaining agent of the present invention can improve or sustain QOL particularly from the physical aspect. In addition, with this, the QOL improving or sustaining agent of the present invention is particularly useful as a physical health improving or sustaining agent. In addition, in more detail, the *Lactobacillus* ONRICb0240 strain has an effect of enhancing vitality, an effect of making fatigue unlikely to occur, and an effect of lessening or alleviating fatigue. Therefore, the QOL improving or sustaining agent of the present invention is also useful as: a vitality improving or sustaining agent; a fatigue recovery agent or a fatigue alleviating agent, particularly, a physical fatigue recovery agent or a physical fatigue alleviating agent; or an anti-fatigue agent.

With the present invention described above, it is possible to prevent or lessen a decline in physical health resulting from disarray of lifestyle factors including insufficient rest and sleep, irregular meal patterns, lack of exercise, intense exercise, aging, and stress. Furthermore, with the present invention described above, shifting to or advancement of a constitutional predisposition of being easily fatigued or chronically fatigued, or a weak constitution can be prevented or suppressed. Still further, with the present invention, even when one has a constitution of easily feeling fatigued such as in the case with a weak constitution, it is possible to prevent worsening of the constitution or to improve the constitution.

From the above described standpoints, the present invention can improve or sustain physical health regardless of age or sex.

MODE FOR CARRYING OUT THE INVENTION

Embodiments of the present invention are set forth in the following.

The QOL improving or sustaining agent of the present invention is characterized by containing *Lactobacillus* ONRICb0240 (FERM BP-10065) strain as an active ingredient. As described above, the QOL improving or sustaining agent of the present invention can be used particularly as a physical health improving or sustaining agent, a vitality improving or sustaining agent, a fatigue recovery agent, a fatigue alleviating agent, an anti-fatigue agent, or the like. Therefore, similarly, these are also characterized by containing the *Lactobacillus* ONRICb0240 strain as an active ingredient.

The *Lactobacillus* ONRICb0240 strain used in the present invention is a *lactobacillus* isolated from a natural source, and was deposited to the International Patent Organism Depositary of National Institute of Advanced Industrial Science and Technology (AIST), which is an independent administrative institution and whose address is Tsukuba Central 6, 1-1-1 Higashi, Tsukuba, Ibaraki, Japan, on Aug. 6, 2003, under an accession number of FERM P-19470. Currently, it has been transferred to the International Depository Authority and has an accession number of FERM BP-10065. The bacteriological nature of the *Lactobacillus* ONRICb0240 strain is known. It should be noted that the *Lactobacillus* ONRICb0240 strain used in the present invention was classified as belonging to *Lactobacillus plantarum* at the time of deposition to the International Depository Authority; however, associated with a later change in the standards for classification (Francois Bringle et al., International Journal of Systematic and Evolutionary Microbiology, Vol. 55, 2005, p. 1629-1634), the present strain is classified as *Lactobacillus pentosus*.

The *Lactobacillus* ONRICb0240 strain, which is contained in the QOL improving or sustaining agent, the physical health improving or sustaining agent, the vitality improving or sustaining agent, the fatigue recovery agent, the fatigue alleviating agent, the anti-fatigue agent, or the like (hereinafter, also represented as the QOL improving or sustaining agent, etc.,) of the present invention, may be in a state of a live bacterium, in a state of a dead bacterium, a processed product of bacterial cells, or in a state of a mixture thereof. Here, a live bacterium is a *lactobacillus* in a live state, also includes: a culture liquid medium of a *lactobacillus*, a suspension, a crude purified product, or a purified product of the culture liquid medium; and bacterial cell powder obtained by drying the live *lactobacillus* with lyophilization, spray drying, or the like, and is not limited as long as it is in a live state. Furthermore, a dead bacterium is a *lactobacillus* in a killed state obtained by performing a chemical treatment or a physical treatment such as heat treatment, radiation treatment, or the like on a *lactobacillus* in a live state, also includes bacterial cell powder obtained by drying the *lactobacillus* in the killed state with lyophilization, spray drying, or the like, and is not limited as long as it is a dead bacterium. Still further, a processed product of bacterial cells is a bacterial cell disruption obtained by disrupting a *lactobacillus* using homogenization, an enzymatic treatment, an ultrasonic treatment, or the like, and also includes powder of the bacterial cell disruption obtained by drying the bacterial cell disruption with lyophilization, spray drying, or the like. The *Lactobacillus* ONRICb0240 strain contained in the QOL improving or sustaining agent, etc. of the present invention is preferably in a state of a live bacterium, a dead bacterium, a processed product of bacterial cells, or a mixture thereof, more preferably is in a state of a dead bacterium, or a mixture of a live bacterium and a dead bacterium, and further preferably is in a state of a dead bacterium.

The *Lactobacillus* ONRICb0240 strain used in the QOL improving or sustaining agent, etc., of the present invention can be grown by culturing thereof in a medium suitable for the growth of the strain. The culturing method is not limited, and, for example, the *Lactobacillus* ONRICb0240 strain can be grown by culturing thereof in a medium such as MRS medium, LBS medium, Rogosa medium, or the like at 30° C. for about 16 hours. Furthermore, after the culturing, bacterial cells can be harvested by, for example, centrifugal separation (e.g., 3,000 rpm, 4° C., 10 minutes) of the culture (culture fluid). Furthermore, the *Lactobacillus* ONRICb0240 strain used in the present invention may be cultured (fermented) in the presence of materials such as milk, vegetables, fruits, soy milk, or the like. Similarly as described above, the bacterial cells can be harvested by centrifugal separation after the culturing. The following can also be used in the present invention: a culture (fermented product) or harvested bacterial cells obtained as described above; a suspension or concentrate of the culture or bacterial cells; or powder obtained by drying the obtained culture, bacterial cells, suspension, or concentrate, using lyophilization, spray drying, or the like. The preparation for them may be performed in accordance with methods commonly known in the art. Furthermore, from the point of more efficiently performing the culturing (fermentation), before fermentation, the materials such as milk, vegetables, fruits, or soy milk preferably have a fluidity equal to or higher than a certain level such as that of a liquid.

As described above, the QOL improving or sustaining agent, etc., of the present invention has to contain the *Lactobacillus* ONRICb0240 strain as an active ingredient. Therefore, for example, as the QOL improving or sustaining agent, etc., the culture may be used without having any processes performed thereon or after having performed thereon a process such as homogenization or the like, or the above described preparation may be used as the QOL improving or sustaining agent, etc.

When the *Lactobacillus* ONRICb0240 strain is contained in the QOL improving or sustaining agent, etc., of the present invention in a live state, from the point of further finely sustaining the live state, it is preferable that the QOL improving or sustaining agent, etc. further contain a nutritional component suitable for the growth of the *Lactobacillus* ONRICb0240 strain in the QOL improving or sustaining agent, etc., as necessary. Such a nutritional component includes respective components of, for example, carbon sources such as glucose, starch, sucrose, lactose, dextrin, sorbitol, fructose, and the like, nitrogen sources such as yeast extract, peptone, and the like, vitamins, minerals, trace metallic elements, and other nutritional components. Specific examples of vitamins include vitamin B, vitamin D, vitamin C, vitamin E, vitamin K, and the like. Specific examples of trace metallic elements include zinc, selenium, and the like. Specific examples of other nutritional components include various oligosaccharides such as lacto-sucrose, soy oligosaccharides, lactulose, lactitol, fructo-oligosaccharides, and galacto-oligosaccharides.

Furthermore, the QOL improving or sustaining agent, etc., of the present invention may contain an optional component as necessary. As the optional component, for example, an edible or pharmaceutically acceptable carrier, additive, or the like may be contained. Examples of the edible or pharmaceutically acceptable carrier or additive include aqueous media, excipients, binders, disintegrants, lubricants, thickening agents, surfactants, osmo-regulators, wetting agents, pH regulators, sweeteners, flavorings, pigments, and the like. These are commonly known for those skilled in the art, and can be appropriately selected to be used. Specific examples thereof include: aqueous media such as water, saline solutions, fruit juices, and the like; excipients such as lactose, white soft sugar, sodium chloride, glucose, urea, starch, calcium carbonate, kaolin, crystalline cellulose, silicic acid, potassium phosphate, corn starch, dextrin, and the like; binders such as water, ethanol, propanol, simple syrup, glucose solutions, starch solutions, gelatin solutions, carboxymethyl cellulose, hydroxypropyl cellulose, methyl cellulose, polyvinylpyrrolidone, and the like; disintegrants such as carboxymethyl cellulose sodium, carboxymethyl cellulose calcium, low substituted hydroxypropyl cellulose, dry starch, sodium alginate, powdered agar, laminaran powder, sodium bicarbonate, calcium carbonate, and the like; lubricants such as purified talc, stearates, boric acid powder, polyethylene glycol, and the like; thickening agents such as gelatin, gum arabic, dextrin, methyl cellulose, polyvinylpyrrolidone, polyvinyl alcohol, hydroxypropyl cellulose, xanthan gum, pectin, tragacanth gum, casein, alginic acid, and the like; surfactants such as polyoxyethylene sorbitan fatty acid esters, sodium lauryl sulfate, stearic monoglyceride, and the like; and sweeteners such as stevia, saccharin, acesulfam K, aspartame, sucralose, and the like.

By those skilled in the art, components that are used as necessary can be appropriately selected, and the blend amount of the components can be adjusted as appropriate so as to conform to an intended form, preference, or the like, as long as the effect of the present invention is not obstructed.

The form of the QOL improving or sustaining agent, etc., of the present invention is not particularly limited, and includes, for example: solid forms such as powder, granules, tablets, pills, troches, and the like; semi-solid forms such as jellies, mousse, yogurt, pudding, and cream; and liquid forms such as liquid agents, suspensions, emulsions, syrups, and the like. Furthermore, these forms may be loaded in a microcapsule, a soft capsule, a hard capsule, or the like, to be made into a capsule form. In addition, the QOL improving or sustaining agent, etc., of the present invention may be made into an effervescent preparation form. The production method of these forms can be conducted in accordance with methods commonly known in the art.

The contained amount of the *Lactobacillus* ONRICb0240 strain in the QOL improving or sustaining agent, etc., of the present invention may be set as appropriate in accordance with a per-day administration dose, an administration mode, the number of administrations, usage purpose, or the like. The contained amount of the *Lactobacillus* ONRICb0240 strain in the QOL improving or sustaining agent, etc., of the present invention is not limited insofar as the effect of the present invention is not adversely affected, and the total number of bacterial cells (i.e., the total number of live bacteria, dead bacteria, processed product of bacterial cells) of the *Lactobacillus* ONRICb0240 strain is, for example, not less than $10^4$ cells/mg, preferably $10^5$ to $10^{12}$ cells/mg, and more preferably $10^6$ to $10^{11}$ cells/mg, based on a single unit of the agent.

Furthermore, the contained amount of the *Lactobacillus* ONRICb0240 strain in the QOL improving or sustaining agent, etc., of the present invention is not limited insofar as the effect of the present invention is not adversely affected, and the total number of bacterial cells of the *Lactobacillus* ONRICb0240 strain in a single unit of the agent is also, for example, not less than $10^4$ cells, preferably $10^6$ to $10^{12}$ cells, more preferably $10^7$ to $10^{12}$ cells, and further preferably $10^8$ to $10^{12}$ cells. From the point of efficiently obtaining the desired effect, the total number of bacterial cells is particularly preferably $10^8$ to $10^{11}$ cells, and the total number of bacterial cells is further preferably $10^9$ to $10^{10}$ cells.

Furthermore, the administration dose of the QOL improving or sustaining agent, etc., of the present invention may be adjusted as appropriate in accordance with age, sex, symptoms, or the like. With regard to the administration dose per day for an adult, the total number of bacterial cells of the *Lactobacillus* ONRICb0240 strain is, for example, not less than $10^4$ cells, preferably $10^6$ to $10^{12}$ cells, more preferably $10^7$ to $10^{12}$ cells, and further preferably $10^8$ to $10^{12}$ cells, and, from the point of efficiently obtaining the desired effect, it is particularly preferably $10^8$ to $10^{11}$ cells, and further preferably $10^9$ to $10^{10}$ cells. The above described dose may be administered once a day, or may be administered in several portions a day. Although the administration method is not limited insofar as the effect of the present invention is not adversely affected, oral administration is preferable.

The total number of bacterial cells of the *Lactobacillus* ONRICb0240 strain may be measured using a bacterial number measuring method or a bacterial number measuring device that are commonly known in the art. For example, as the bacterial number measuring device commonly known in the art, a microscope, a flow cytometer, or a Rapid Microbe Measuring System BIOPLORER (Registered Trademark) (product of Panasonic Ecology Systems Co., Ltd.) can be used. In Examples described later, the total number of bacterial cells was measured using a flow cytometer at a stage when lyophilized bulk powder was produced.

Furthermore, an application subject of the present invention is not limited as long as it is an animal whose object is to improve or sustain QOL through improving or sustaining physical health. Examples of the animal include mammals such as human; however, in addition thereto, various animals such as pets and livestock other than mammals may be included. There is no limitation in the age or sex of the application subject of the present invention.

The QOL improving or sustaining agent, etc., of the present invention can be applied to food or a beverage. More specifically, the QOL improving or sustaining agent, etc., of the present invention can be used as an additive to food or a beverage. With such food or beverage containing the QOL improving or sustaining agent, etc., of the present invention, the effect resulting from the QOL improving or sustaining agent, etc., of the present invention, i.e., the effect resulting from the *Lactobacillus* ONRICb0240 strain, can be obtained. Furthermore, the QOL improving or sustaining agent, etc., of the present invention can be directly used as a pharmaceutical preparation. In addition, the QOL improving or sustaining agent, etc., of the present invention can be used as an additive to a pharmaceutical preparation. With such a pharmaceutical preparation containing the QOL improving or sustaining agent, etc., of the present invention, the effect resulting from the QOL improving or sustaining agent, etc., of the present invention, i.e., the effect resulting from the *Lactobacillus* ONRICb0240 strain, can be obtained.

When the QOL improving or sustaining agent, etc., of the present invention is applied in a food, beverage, or pharmaceutical preparation, the type of the food, beverage, or pharmaceutical preparation is not limited, and the *Lactobacillus* ONRICb0240 strain may be blended in the food, beverage, or pharmaceutical preparation as one component. Furthermore, in accordance with needs, an optional component may be further contained therein, such as, for example, an edible or pharmaceutical acceptable carrier, additive, or the like. Examples of the edible or pharmaceutically acceptable carrier, additive, or the like include, but not limited to, the above described aqueous media, excipients, binders, disintegrants, lubricants, thickening agents, surfactants, osmo-regulators, wetting agents, pH regulators, sweeteners, flavorings, pigments, and the like. By those skilled in the art, these components can be appropriately selected, and the blend amount of the components can be adjusted as appropriate so as to conform to an intended form, preference, or the like, as long as the effect of the present invention is not obstructed.

The food, beverage, or pharmaceutical preparation containing the QOL improving or sustaining agent, etc., of the present invention is also not limited as long as the effect of the present invention is exerted. The food and beverage include, but not limited to, for example, snacks (gum, candies, cookies, gummy candies, rice crackers, biscuits, jelly, mousse, cream caramels, carbonated candies, edible sheets, edible films, troches, etc.), mouth deodorants (gum, candies, gummy candies, edible films, troches, etc.), beverages (carbonated beverages, soft drinks, milk beverages, alcoholic beverages, fruit juice drinks, tea, energy drinks, etc.), powdered beverages (powdered juices, powdered soups, etc.), dairy products (cheese, yogurt, etc.), bread, noodles, cereals, and the like. Furthermore, the food and beverage may include, for example, food for specified health use, dietary supplements, food products for the sick, and the like. Still further, the pharmaceutical preparation is also not limited, and includes the above described preparations in solid forms, semi-solid forms, or liquid forms, capsules, effervescent preparations, and the like. The production method of these can be conducted in accordance with methods commonly known in the art.

The contained amount of the *Lactobacillus* ONRICb0240 strain in the food, beverage, or pharmaceutical preparation containing the QOL improving or sustaining agent, etc., of the present invention may be set as appropriate in accordance with a per-day administration dose, an administration mode, the number of administrations, usage purpose, or the like. The total number of bacterial cells of the *Lactobacillus* ONRICb0240 strain in the food, beverage, or pharmaceutical preparation is, for example, not less than $10^4$ cells/mg, preferably $10^5$ to $10^{12}$ cells/mg, and more preferably $10^6$ to $10^{11}$ cells/mg, based on a single unit of the food, beverage, or pharmaceutical preparation, however it is not limited thereto insofar as the effect of the present invention is not adversely affected.

Furthermore, the contained amount of the *Lactobacillus* ONRICb0240 strain in the food, beverage, or pharmaceutical preparation is not limit insofar as the effect of the present invention is not adversely affected, and the total number of bacterial cells of the *Lactobacillus* ONRICb0240 strain in a single unit of the food, beverage, or pharmaceutical preparation is also, for example, not less than $10^4$ cells, preferably $10^6$ to $10^{12}$ cells, more preferably $10^7$ to $10^{12}$ cells, and further preferably $10^8$ to $10^{12}$ cells. From the point of efficiently obtaining the desired effect, the total number of bacterial cells is particularly preferably $10^8$ to $10^{11}$ cells, and the total number of bacterial cells is further preferably $10^9$ to $10^{10}$ cells.

Furthermore, the administration dose of the food, beverage, or pharmaceutical preparation may be adjusted as appropriate in accordance with age, sex, symptoms, or the like. With regard to a per-day administration dose for an adult, the total number of bacterial cells of the *Lactobacillus* ONRICb0240 strain is, for example, not less than $10^4$ cells, preferably $10^6$ to $10^{12}$ cells, more preferably $10^7$ to $10^{12}$ cells, further preferably $10^8$ to $10^{12}$ cells, and, from the point of efficiently obtaining the desired effect, it is particularly preferably $10^8$ to $10^{11}$ cells, and further preferably $10^9$ to $10^{10}$ cells. The above described dose may be administered once a day, or may be administered in several portions a day.

As described above, the *Lactobacillus* ONRICb0240 strain can effectively promote improvement or sustainment of QOL, etc. Thus, the present invention further provides a method for improving or sustaining QOL, etc. using the *Lactobacillus* ONRICb0240 strain. The method for improving or sustaining QOL, etc. of the present invention can be conducted by administering the *Lactobacillus* ONRICb0240 strain to an animal seeking improvement or sustainment of QOL, or the like. That is, the present invention's method for improving or sustaining QOL, etc. of the present invention includes a step of causing an animal that requires improvement or sustainment of QOL, or the like, to take in the QOL improving or sustaining agent, or the food, beverage, or pharmaceutical preparation containing the QOL improving or sustaining agent. For the method of the present invention, administration dose, the number of administrations, method of administration, site of administration, and the like for the *Lactobacillus* ONRICb0240 strain, the QOL improving or sustaining agent, or the food, beverage, or pharmaceutical preparation containing the QOL improving or sustaining agent, are determined in accordance with the description above.

As described above, the QOL improving or sustaining agent of the present invention can improve or sustain QOL. In particular, the QOL improving or sustaining agent of the present invention has an effect of enhancing physical health. Thus, the QOL improving or sustaining agent can improve or sustain QOL particularly from the physical aspect, and thereby can be used as a physical health improving or sustaining agent. Furthermore, the QOL improving or sustaining agent of the present invention has, in particular, an effect of enhancing vitality, an effect of lessening and alleviating fatigue, and an effect of making fatigue unlikely to occur. Therefore, the QOL improving or sustaining agent can also be used as: a vitality improving or sustaining agent; a fatigue recovery agent or a fatigue alleviating agent, particularly, a physical fatigue recovery agent or a physical fatigue alleviating agent; an anti-fatigue agent; or the like.

With the present invention described above, it is possible to prevent or lessen a decline in physical health resulting from disarray of lifestyle factors including insufficient rest and sleep, irregular meal patterns, lack of exercise, intense exercise, aging, and stress. Furthermore, with the present invention described above, shifting to or advancement of a constitutional predisposition of being easily fatigued or chronically fatigued, or a weak constitution can be prevented or suppressed. Still further, with the present invention, even when one has a constitution of easily feeling fatigued such as in the case with a weak constitution, it is possible to prevent worsening of the constitution or to improve the constitution. That is, the present invention is applicable when seeking improvement or sustainment in physical health, and thus is obviously applicable to healthy people who do not require any treatments from a medical standpoint, and outpatients living lives similar to healthy people. Furthermore, the present invention can achieve improvement or sustainment of QOL from the physical aspect as described above, and thereby it can, although indirectly, improve or sustain mental health affected by stress and inconvenience in everyday life resulting from a decline in physical health. Therefore, the present invention enables to sustain both physical and mental aspects in a fine condition, which is strongly sought in the present day.

In particular, with the present invention, as shown in the Examples described later, QOL based on physical health has been significantly improved in study subjects having physical health more superior than that of the ordinary. Generally, since such study subjects are extremely healthier than the ordinary, significant differences hardly appear in terms of the effect. However, even under such circumstance, a significant improving effect has been seen in the later described Examples. This clearly indicates that the QOL improving or sustaining effect of the present invention from the physical aspect is significantly superior. It should be noted that, in the Examples, the effect was evaluated based on SF-36v2 (Registered Trademark). SF-36 (Registered Trademark) is a scale that is valid, reliable, and scientific and is widely used internationally for measuring health-related QOL. SF-36v2 (Registered Trademark) is an improvement over SF-36

(Registered Trademark). Details of SF-36v2 (Registered Trademark) are described in SF-36v2™ Japanese version manual published by, an NPO, the Institute for Health Outcomes & Process Evaluation research, on October 2009.

EXAMPLES

In the following, the present invention will be described using Examples; however, the present invention is not limited to those Examples.

Example 1: QOL Improving or Sustaining Agent

Two types of QOL improving or sustaining agents having different contained amounts of the *Lactobacillus* ONRICb0240 strain were produced in accordance with the following procedure.

Cultured *Lactobacillus* ONRICb0240 strain was collected using centrifugal separation and suspended in distilled water, and a lyophilization process was performed thereon to obtain lyophilized bulk powder of the *Lactobacillus* ONRICb0240 strain. The number of bacteria in the bulk powder was counted using a flow cytometer (EPICS (registered trademark) XL-MCL, product of Beckman Coulter, Inc.) in accordance with a manual. Then, the *Lactobacillus* ONRICb0240 strain was added to an excipient so as to achieve $4 \times 10^9$ cells/tablet, and a tablet was produced using a high-speed, rotary, small-sized research tablet machine (VIRG 0512SS2AZ, product of KIKUSUI SEISAKUSHO Ltd.). This is referred to as Composition 1. Furthermore, another tablet was produced similarly, except that the *Lactobacillus* ONRICb0240 strain was $4 \times 10^{10}$ cells/tablet. This is referred to as Composition 2.

The QOL improving or sustaining agent obtained as described above can be used as a physical health improving or sustaining agent, a vitality improving or sustaining agent, a fatigue recovery agent, a fatigue alleviating agent, an anti-fatigue agent, or the like.

Experimental Example 1

1. Study Method

Prior to Study, elderly people aged 65 or older (age: 65-84) from whom informed concent were acquired voluntarily were selected as study subjects. The age and sex ratio of the subjects were adjusted as appropriate, and 300 subjects were randomly allocated into 3 groups, each containing 100 subjects.

Three patterns were prepared as objects to be tested: a placebo composition, Composition 1 (containing $4 \times 10^9$ cells of the *Lactobacillus* ONRICb0240 strain) produced in Example 1, and Composition 2 (containing $4 \times 10^{10}$ cells of the *Lactobacillus* ONRICb0240 strain) produced in Example 1. The placebo composition was produced similarly to Compositions 1 and 2, except for not using the *Lactobacillus* ONRICb0240 strain.

A group administered with the placebo composition is referred to as "group (I)," a group administered with the composition containing $4 \times 10^9$ cells of the *Lactobacillus* ONRICb0240 strain is referred to as "group (II)," and a group administered with the composition containing $4 \times 10^{10}$ cells of the *Lactobacillus* ONRICb0240 strain is referred to as "group (III)."

For each of the groups, the administration of the objects to be studied was performed such that one tablet was taken every day for 20 consecutive weeks. The tastes and the colors of the objects to be studied were made identical, and identical packaging containers were used. It should be noted that the study was performed so as to be a randomized double-blind, placebo-controlled trial was conducted between parallel groups.

In addition, at the beginning and end of the study, a total of 36 questions were asked for measuring effects on eight health concepts (subscale) using a SF-36v2 questionnaire form. Answers to the questions were obtained as a review of health conditions in the previous month.

The obtained answers were processed in accordance with the manual for SF-36v2 (registered trademark). Specifically, they were processed in accordance with the SF-36v2™ Japanese version manual published by the Institute for Health Outcomes & Process Evaluation Research, an NPO, in October 2009. Described briefly, raw scores were calculated in accordance with the manual from the answers obtained with regard to each of the health concepts (subscales) and were converted into subscale scores ranging from 0 to 100 points. For each of the health concepts, a value obtained by subtracting an average of subscale scores obtained at the beginning of the study from an average of subscale scores obtained at the end of the study was shown as a delta value ($\Delta$ value), and delta values were compared between groups. The comparison between groups was conducted using the Dunnett test, and dose dependency was evaluated using the Jonckheere trend test (two-tailed test).

At the very end, evaluation was conducted based on the results obtained from 93 subjects in group (I), 92 subjects in group (II), and 93 subjects in group (III).

2. Study Results

A comparison between averages (physical healthiness scores) of the subscale scores for the study subjects before study and the averages from nationwide survey sampling is shown in Table 1. SF-36v2 can evaluate eight health concepts (subscales), which are physical functioning PF, role physical RP, bodily pain BP, general health GH, vitality VT, social functioning SF, role emotional RE, and mental health MH. It has been determined that five of these items, which are physical functioning PF, role physical RP, bodily pain BP, general health GH, and vitality VT, are involved in physical health (physical healthiness). Therefore, in the present Experimental Example, evaluation was conducted mainly on these five health concepts. Here, the averages from nationwide survey sampling are the values described as national averages for Japanese on page 101 of the SF-36v2™ Japanese version manual published by the Institute for Health Outcomes & Process Evaluation Research, an NPO, in October 2009.

TABLE 1

Comparison of physical healthiness scores of study subjects at the beginning of study and averages from nationwide survey sampling

| | | Physical functioning PF | Role Physical RP | Bodily pain BP | General health GH | Vitality VT |
|---|---|---|---|---|---|---|
| Averages from nationwide survey sampling | Overall | 89.1 | 89.2 | 73.8 | 62.9 | 62.8 |
| | Age: 60-69 | 84.9 | 87.3 | 73.1 | 60.7 | 67.0 |
| | Age: 70-79 | 74.9 | 78.0 | 66.1 | 58.4 | 64.9 |
| Averages of study subjects at the beginning of study | Group (I) | 91.1 | 92.9 | 76.0 | 72.0 | 76.6 |
| | Group (II) | 92.1 | 93.1 | 81.6 | 70.9 | 78.0 |
| | Group (III) | 90.8 | 92.2 | 78.1 | 73.2 | 78.2 |

As is obvious from Table 1, when the scores of the study subjects and the averages from nationwide survey sampling were compared, the study subjects showed significantly higher values in all the evaluation items. Although the study subjects in the present Experimental Example were elderly people aged 65 or older (age: 65-84), their values were markedly better than the averages of nationwide survey sampling of people aged 60 or older (age: 60-69 and 70-79). Furthermore, the values of the study subjects in the present Experimental Example were better even when compared to standard values (overall) from nationwide survey sampling of an average age of 50.5, and the study subjects scored highly particularly in general health GH and vitality VT. Therefore, it was determined that the study subjects in the present Experimental Example were significantly healthier than the national average.

Normally when evaluating influences on physical health improvement, effects on healthy people hardly appear since they are healthy to begin with. Therefore, it was predicted that in the present Experimental Example with study subjects who were extremely healthy, significant differences would hardly occur in groups (I) to (III) with regard to improvement in QOL based on physical health, particularly with regard to improving effects of general health, vitality, etc. However, unexpectedly, significant differences were confirmed in groups (I) to (III) as shown in the following.

Scores for general health GH before and at the end of the study ($20^{th}$ week) from groups (I) to (III) were compared. The results are shown in Table 2.

TABLE 2

Score comparison of general health GH before and at the end of the study

|  |  | Before study | At the end of study | Delta value |
|---|---|---|---|---|
| Score averages | Group (I) | 72.0 | 69.3 | −2.6 |
|  | Group (II) | 70.9 | 72.1 | 1.2 |
|  | Group (III) | 73.2 | 75.2 | 2.0 |

Shown in Table 2 are scores at the beginning of the study, scores at the end of the study, and differences (delta value: value obtained by subtracting the score before study from the score at the end of the study) between scores at the beginning and end of the study.

As described above, the study subjects were all healthier than elderly people around the same age and healthier than the national average; therefore, it was predicted that differences would hardly occur in groups (I) to (III) with regard to improvement effects on physical health. However, group (II) and group (III) showed higher scores when compared to group (I).

Furthermore, the twentieth week, which is when the study was ended, was summer, and thus it was predicted that general health would be reduced even for healthy study subjects. In fact, as is obvious from Table 2, in group (I), which is the placebo composition administration group, the score at the end of the study was reduced by 2.6 from the score obtained at the beginning of the study. As this indicates, since the season was one in which general health is easily impaired, it would have been satisfactory if the scores at the beginning of the study were at best maintained in group (II) and group (III); therefore, the situation allowed evaluating that a sufficiently satisfactory effect was obtained if the scores were maintained. However, as is obvious from Table 2, in group (II) and group (III), not only were the scores maintained, but the scores at the end of the study exceeded the scores at the beginning of the study.

In addition, since the delta value was larger in group (III) when compared to group (II), it became clear that general health is enhanced with the *Lactobacillus* ONRICb0240 strain in a dosage-dependent manner.

From the above-described results, it was shown that general health can be significantly improved with the *Lactobacillus* ONRICb0240 strain.

Furthermore, scores for vitality VT were similarly compared between groups (I) to (III). Table 3 shows the number of study subjects whose scores for vitality VT before study worsened by 20 or more (−20) when compared to the scores at the end of the study.

TABLE 3

Comparison of numbers of study subjects whose scores for vitality VT worsened by 20 or more

|  | Number of test subjects |
|---|---|
| Group (I) | 14 people |
| Group (II) | 10 people |
| Group (III) | 7 people |

As is obvious from Table 3, the number of study subjects whose scores for vitality VT worsened by 20 or more was as large as 14 in group (I), and was sequentially reduced to 10 and 7 in group (II) and group (III).

As described above, the study subjects were all extremely healthier than the national average, and the time when the study was conducted was a season in which physical strength can easily deteriorate. Regardless of such circumstances, the fact that such a significant difference was observed indicated that vitality can be significantly improved by taking the *Lactobacillus* ONRICb0240 strain.

Given in the SF-36v2™ Japanese version manual is a table that compiles the relation of the score (score-sorted category) for vitality VT, proportion of people who answered "always" and "almost always" feeling full of vitality, and proportion of people who answered as feeling fatigued (p. 132, Table 11.2). A partial excerpt of the table is shown in the following as Table 4.

TABLE 4

Partial excerpt of Table 11.2 on p.132 of SF-36v2 ™ Japanese version manual

| Score-sorted category | Average VT | Number of subjects | People with vitality (%) | Fatigued people (%) |
|---|---|---|---|---|
| 100 | 100.0 | 89 | 100% | 0.0% |
| 90-99 | 93.7 | 77 | 100% | 0.0% |
| 80-89 | 83.9 | 329 | 93.9% | 0.1% |
| 70-79 | 75.0 | 309 | 84.0% | 2.3% |
| 60-69 | 65.6 | 546 | 49.9% | 2.4% |
| 50-59 | 53.1 | 513 | 12.2% | 17.1% |

With regard to this table, for example, a classification of score-sorted category 80-89 indicates that among the 329 people belonging to this score-sorted category, 93.9% answered as feeling full of vitality, and 0.1% answered as feeling fatigued.

In the present Experimental Example, the average of the score-sorted category related to vitality VT before the testing for the study subjects was 70. From this it can be said that the study subjects were a group in which 84% felt full of vitality and 2.3% felt fatigued before the study. In this group, if the score after the end of the study worsened by 20, the score-sorted category would have shifted down to 50-59. As is obvious from Table 4, the score-sorted category 50-59 indicates that the group was one in which 12.2% felt full of vitality and 17.1% felt fatigued. As shown here, to have a score worsen by 20 in the present test means that a proportion feeling full of vitality was significantly reduced from 84% to 12.2%, and a proportion feeling fatigued was significantly increased from 2.3% to 17.1%. To suppress such a worsening is extremely important.

As is obvious from the above-described Table 3, worsening of the score by 20 or more was suppressed in group (II) and group (III) when compared to group (I). Thus, considering a comparison of Table 3 and Table 4, it was shown that in group (II) and group (III), unexpectedly, deterioration in vitality was effectively suppressed and an effect of alleviation of or recovery from physical fatigue was exerted.

Scores for role physical RP were similarly compared between groups (I) to (III). Table 5 shows the number of study subjects whose scores for role physical RP before testing worsened by 20 or more (−20) when compared to the scores at the end of the study.

TABLE 5

Comparison of number of study subjects whose scores for role physical RP worsened by 20 or more

| | Number of study subjects |
|---|---|
| Group (I) | 12 people |
| Group (II) | 10 people |
| Group (III) | 6 people |

As is obvious from Table 5, the number of study subjects whose scores for role physical RP worsened by 20 or more was 12 in group (I); however, it was sequentially reduced to 10 and 6 in group (II) and group (III). Role physical RP is a scale that evaluates increase/decrease of everyday activity time and the ability/disability of everyday activity. As shown here, since worsening of the score was able to be suppressed also for role physical RP, it was shown that taking the Lactobacillus ONRICb0240 strain allows reducing the possibility of an occurrence of a physical problem that may interfere with work and everyday activities.

Furthermore, as described above, physical health (physical healthiness) is evaluated by using five health concepts (the five items being physical functioning PF, role physical RP, bodily pain BP, general health GH, and vitality VT). Therefore, scores regarding the five health concepts were similarly compared between groups (I) to (III). Specifically, with regard to physical health (physical healthiness) evaluated by using the five health concepts, Table 6 shows the number of study subjects whose scores worsened in two or more of the health concepts by 10 or more, or 20 or more at the end of the study when compared to before study.

TABLE 6

Comparison of number of study subjects whose scores for physical health (physical healthiness) worsened by 10 or more, or 20 or more

| | Number of study subjects whose scores worsened by 10 or more in two or more items | Number of study subjects whose scores worsened by 20 or more in two or more items |
|---|---|---|
| Group (I) | 41 people | 16 people |
| Group (II) | 33 people | 11 people |
| Group (III) | 32 people | 6 people |

As is obvious from Table 6, with regard to physical health (physical healthiness), the number of study subjects whose scores worsened by 10 or more in two or more items and the number of study subjects whose scores worsened by 20 or more in two or more items were greatly reduced in group (II) and group (III) when compared to group (I). This showed that taking the Lactobacillus ONRICb0240 strain significantly improves physical health.

From these results, it became clear that the Lactobacillus ONRICb0240 strain is useful for improvement or sustainment of physical health, particularly for improvement or sustainment of QOL in physical aspects, such as vitality improvement or sustainment, recovery from physical fatigue, physical fatigue alleviation, and anti-fatigue.

The invention claimed is:

1. A quality of life (QOL) improving or sustaining method for a human, the method comprising a step of administering a QOL improving or sustaining agent containing Lactobacillus ONRIC b0240 (FERM BP-10065) to the human,
wherein the QOL improvement or sustainment is at least one physical health improvement or sustainment selected from the group consisting of vitality improving, vitality sustaining, fatigue recovery, fatigue alleviating, anti-fatigue and general health improving or sustaining,
wherein the general health improving or sustaining is measured based on a 36-Item Short Form Survey, and
wherein the human is a healthy human who does not require treatment or an outpatient living life similar to the healthy human.

2. The method according to claim 1, wherein the administering QOL improving or sustaining agent is administering a food, beverage or a pharmaceutical preparation containing the agent to the human.

3. The method according to claim 1, wherein the human is a human that requires the improvement or sustainment of QOL.

4. The method according to claim 1, wherein Lactobacillus ONRIC b0240 (FERM BP-10065) is in dead state.

* * * * *